United States Patent
Mukhopadhyay et al.

(10) Patent No.: US 11,490,824 B2
(45) Date of Patent: Nov. 8, 2022

(54) METHOD AND SYSTEM FOR HEART RATE ESTIMATION OF A USER

(71) Applicant: Tata Consultancy Services Limited, Mumbai (IN)

(72) Inventors: Shalini Mukhopadhyay, Kolkata (IN); Nasimuddin Ahmed, Kolkata (IN); Arijit Chowdhury, Kolkata (IN); Varsha Sharma, Kolkata (IN); Avik Ghose, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 17/013,274

(22) Filed: Sep. 4, 2020

(65) Prior Publication Data
US 2021/0068686 A1 Mar. 11, 2021

(30) Foreign Application Priority Data
Sep. 6, 2019 (IN) .............................. 201921035986

(51) Int. Cl.
*A61B 5/024* (2006.01)
*A61B 5/00* (2006.01)

(52) U.S. Cl.
CPC .......... *A61B 5/02416* (2013.01); *A61B 5/721* (2013.01); *A61B 5/7264* (2013.01); *A61B 2562/0219* (2013.01)

(58) Field of Classification Search
CPC .................. A61B 5/721; A61B 5/7264; A61B 2562/0219; A61B 5/02416
See application file for complete search history.

(56) References Cited

U.S. PATENT DOCUMENTS

| | | | |
|---|---|---|---|
| 2016/0022220 A1* | 1/2016 | Lee | A61B 5/02433 600/479 |
| 2016/0302679 A1* | 10/2016 | De Haan | A61B 5/02416 |
| 2019/0192079 A1* | 6/2019 | Groenendaal | A61B 5/7253 |

OTHER PUBLICATIONS

"Statistics—Trimmed Mean", Sep. 21, 2015, tutorialspoint (Year: 2015).*

(Continued)

*Primary Examiner* — Christian Jang
*Assistant Examiner* — Anna Roberts
(74) *Attorney, Agent, or Firm* — Finnegan, Henderson, Farabow, Garrett & Dunner, LLP

(57) ABSTRACT

While performing heart rate estimation of a user, if the user is in motion, a signal is measured and is likely to have noise data, which in turn affects accuracy of estimated heart rate value. Method and system for heart rate estimation when the user is in motion is disclosed. The system estimates value of a noise signal present in a measured PPG signal by performing a Principal Component Analysis (PCA) of an accelerometer signal collected along with the PPG signal. The system further estimates value of a true cardiac signal for a time window, based on value of the true cardiac signal in a pre-defined number of previous time windows. The system then estimates frequency spectrum of a clean PPG signal based on the estimated noise signal and the true cardiac signal. The system further performs heart rate estimation based on the clean PPG signal.

9 Claims, 3 Drawing Sheets

(56) References Cited

OTHER PUBLICATIONS

Temko, A., "Estimation of Heart Rate from Photoplethysmography during Physical Exercise using Wiener Filtering and the Phase Vocoder", 2017 IEEE International Conference on Acoustics, Speech and Signal Processing (ICASSP), 2017, IEEE, https://cora.ucc.ie/bitstream/handle/10468/5554/4916.pdf?sequence=1&isAllowed=y.
Dubey, Harishchandra et al., Harmonic Sum-based Method for Heart Rate Estimation using PPG Signals Affected with Motion Artifacts, Journal of Ambient Intelligence and Humanized Computing, Oct. 2016, Research Gate, https://digitalcommons.uri.edu/cgi/viewcontent.cgi?article=1067&context=ele_facpubs.

\* cited by examiner

METHOD AND SYSTEM FOR HEART RATE ESTIMATION OF A USER

PRIORITY CLAIM

This U.S. patent application claims priority under 35 U.S.C. § 119 to: India Application No. 201921035986, filed on Sep. 6, 2019. The entire contents of the aforementioned application are incorporated herein by reference.

TECHNICAL FIELD

The disclosure herein generally relates to heart rate estimation, and, more particularly, to a method and system for heart rate estimation when the user is in motion.

BACKGROUND

Heart rate estimation is process of estimating heart rate of a user using appropriate sensor(s). The estimated heart rate may be used for determining a health condition of the user. For example, with advancement in the field of wearable technology, many of the wearable gadgets available in the market have heart rate estimation capability as one of the features. Many of such gadgets can be configured to trigger an alert to one or more users when an abnormal variation in the heart rate of a user is detected, thereby enabling the user to seek medical help when needed.

The inventors here have recognized several technical problems with such conventional systems, as explained below. Many types of sensors and systems are currently available for performing the heart rate estimation. Photoplethysmogram (PPG) is an example of sensors that can be used for the heart rate estimation. The PPG can monitor the heart rate of a user by measuring variation in blood volume in skin of the user, which is caused by pressure pulse of cardiac signal. However, when the user being monitored is in motion, there is high probability that the measured signals contain noise signals, which in turn affects accuracy of the heart rate estimation being performed. The state of art systems use different approaches for estimating the heart rate of users. However, depending on the approach used, capability to handle the noise caused by the user motion varies, which in turn affects accuracy of result of the heart rate estimation.

SUMMARY

Embodiments of the present disclosure present technological improvements as solutions to one or more of the above-mentioned technical problems recognized by the inventors in conventional systems. For example, in one embodiment, a processor implemented method for heart rate estimation is provided. In this method, a Photoplethysmogram (PPG) signal is collected over a plurality of fixed time windows from a user being monitored, via one or more hardware processors. Further, it is determined whether the user was in motion while the PPG signal in each time window was being collected, by performing a mobility detection, via the one or more hardware processors, and further, each of the plurality of time windows is classified as belonging to one of a set of time windows in which user is determined as in motion and a set of time windows in which user is determined as not in motion. Further, the heart rate estimation is performed for the PPG signal collected over each time window in which the user is determined to be in motion, via the one or more hardware processors. During the heart rate estimation, a noise signal is estimated by performing a Principal Component Analysis (PCA) of an accelerometer signal collected over each of the time windows in which the user is determined as being in motion. Further, value of a true cardiac signal is estimated for each of the time windows in which the user is determined as being in motion, as a trimmed mean of an obtained pre-defined number of spectra prior to a time window being considered. Further, a spectrum of a clean PPG signal is obtained based on the estimated noise signal and the estimated value of the true cardiac signal, using a Wiener filter, and then the heart rate of the user is estimated based on the estimated spectrum of the clean PPG signal.

In another aspect, a system for heart rate estimation is provided. The system includes one or more hardware processors, one or more communication interfaces, and one or more memory storing a plurality of instructions. The plurality of instructions when executed cause the one or more hardware processors to collect a Photoplethysmogram (PPG) signal over a plurality of fixed time windows from a user being monitored, via one or more hardware processors. Further, the system determines whether the user was in motion while collecting the PPG signal, by performing a mobility detection, and further, each of the plurality of time windows is classified as belonging to one of a set of time windows in which user is determined as in motion and a set of time windows in which user is determined as not in motion. The system then performs the heart rate estimation for the PPG signal collected over each time window in which the user is determined to be in motion. In this step, the system estimates a noise signal by performing a Principal Component Analysis (PCA) of an accelerometer signal collected over each of the time windows in which the user is determined as being in motion. The system then estimates value of a true cardiac signal for each of the time windows in which the user is determined as being in motion as equal to trimmed mean of obtained pre-defined number of spectra prior to a time window being considered, from a Clean Signal Buffer (CBF). The system then estimates spectrum of a clean PPG signal based on the estimated noise signal and the estimated value of the true cardiac signal, using a Wiener filter. Further, based on the estimated spectrum of the clean PPG signal, heart rate estimation of the user is performed.

In yet another aspect, a non-transitory computer readable medium for heart rate estimation of a user is provided. The non-transitory computer readable medium executes the following method for the heart rate estimation of the user. In this method, a Photoplethysmogram (PPG) signal is collected over a plurality of fixed time windows from a user being monitored, via one or more hardware processors. Further, it is determined whether the user was in motion while the PPG signal in each time window was being collected, by performing a mobility detection, via the one or more hardware processors, and further, each of the plurality of time windows is classified as belonging to one of a set of time windows in which user is determined as in motion and a set of time windows in which user is determined as not in motion. Further, the heart rate estimation is performed for the PPG signal collected over each time window in which the user is determined to be in motion, via the one or more hardware processors. During the heart rate estimation, a noise signal is estimated by performing a Principal Component Analysis (PCA) of an accelerometer signal collected over each of the time windows in which the user is determined as being in motion. Further, value of a true cardiac signal is estimated for each of the time windows in which the user is determined as being in motion, as a trimmed mean of an obtained pre-defined number of spectra prior to a time window being considered. Further, a spectrum of a clean PPG signal is obtained based on the estimated noise signal and the estimated value of the true cardiac signal, using a Wiener filter, and then the heart rate of the user is estimated based on the estimated spectrum of the clean PPG signal.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
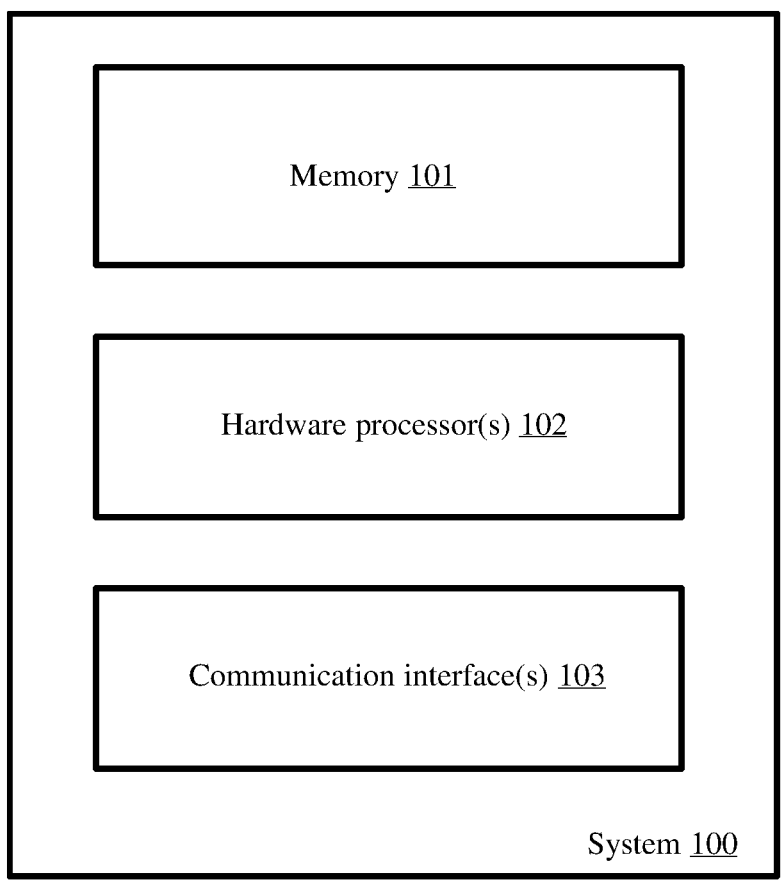
FIG. 1 illustrates an exemplary system for heart rate estimation of a user, according to some embodiments of the present disclosure.
Figure 2:
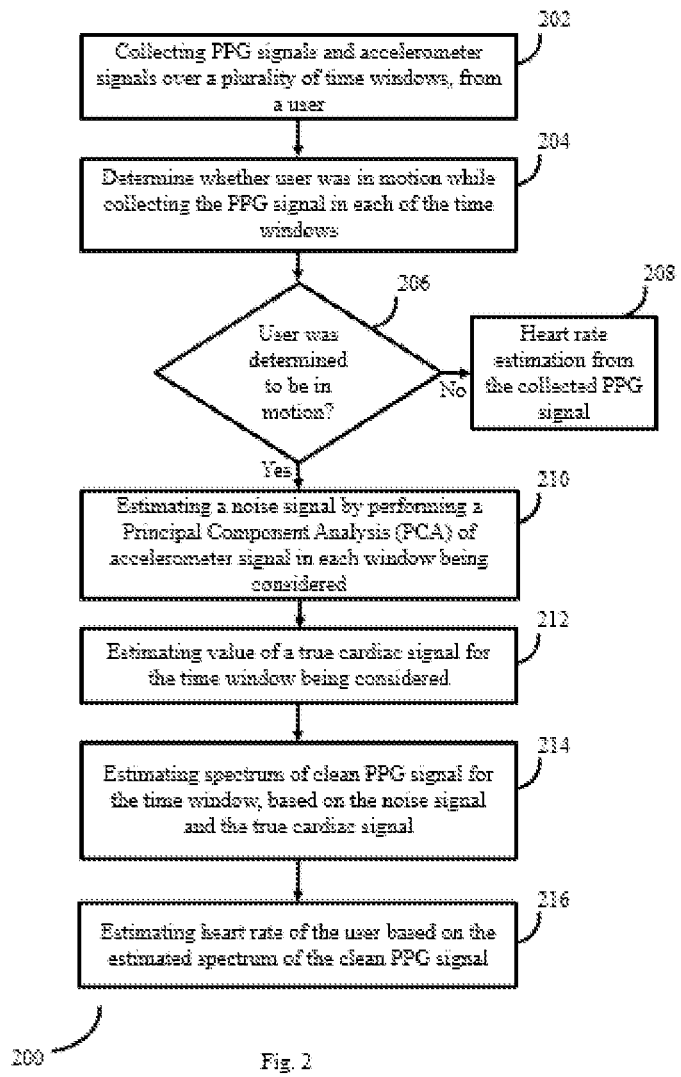
FIG. 2 is a flow diagram depicting steps involved in the process of performing the heart rate estimation, using the system of FIG. 1, according to some embodiments of the present disclosure.
Figure 3:
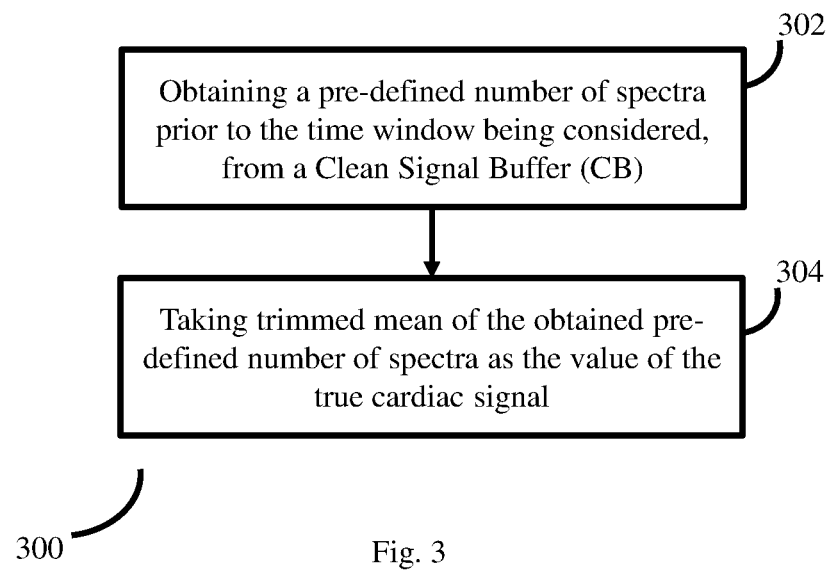
FIG. 3 is a flow diagram depicting steps involved in the process of performing estimating a true cardiac signal for the purpose of performing the heart rate estimation using the system of FIG. 1, according to some embodiments of the present disclosure.

Referring now to the drawings, and more particularly to FIG. 1 through FIG. 3, where similar reference characters denote corresponding features consistently throughout the figures, there are shown preferred embodiments and these embodiments are described in the context of the following exemplary system and/or method.

FIG. 1 illustrates an exemplary system for heart rate estimation of a user, according to some embodiments of the present disclosure. The system 100 includes one or more hardware processors 102, communication interface(s) or input/output (I/O) interface(s) 103, and one or more data storage devices or memory 101 operatively coupled to the one or more hardware processors 102. The one or more hardware processors 102 can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The communication interface(s) 103 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the communication interface(s) 103 can include one or more ports for connecting a number of devices to one another or to another server.

The memory 101 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more components (not shown) of the system 100 can be stored in the memory 101. The memory 101 is configured to store operational instructions which when executed cause one or more of the hardware processor(s) 102 to perform various actions associated with the heart rate estimation being handled by the system 100. The various steps involved in the process of heart rate estimation are explained with description of FIG. 2 and FIG. 3. All the steps in FIG. 2 and FIG. 3 are explained with reference to the system of FIG. 1.

FIG. 2 is a flow diagram depicting steps involved in the process of performing the heart rate estimation, using the system of FIG. 1, according to some embodiments of the present disclosure. So as to perform heart rate estimation of a user, the one or more hardware processors 102 of the system 100 collects (202) PPG signals and accelerometer signals from the user, wherein the collected PPG signals and accelerometer signals are split over a plurality of time windows. In an embodiment, length of all the time windows is same. In various other embodiments, the length of the time windows is pre-configured or dynamically configured with the system 100, by any authorized user, using appropriate interface that may be provided by the communication interface(s) 103. The one or more hardware processors 102 of the system 100 may perform appropriate pre-processing to clean up and condition the collected PPG and accelerometer signals for further processing for the heart rate estimation, and may perform filtering and normalization.

For each time window in which the PPG signal has been collected, the one or more hardware processors 102 of the system 100 performs a mobility detection to determine (204) whether or not the user was in motion while the PPG signal was collected. In an embodiment, any suitable mobility detection mechanism can be used by the system 100 to perform the mobility detection. If the user is found to be not in motion while collecting the PPG signals, then heart rate estimation is performed (208) from the collected PPG signals using any suitable approach.

If the system 100 determines (206) that the user was in motion while collecting the PPG signals in at least one of the plurality of time windows, then the following method is executed for the heart rate estimation. The method is explained for data (i.e. PPG signal and accelerometer signals) collected over one time window. It is to be noted that the same approach is used for heart rate estimation in all time windows in which user was determined to be in motion while collecting the PPG signals.

The one or more hardware processors 102 of the system 100 collects and processes the accelerometer signal in the time window being considered, to estimate (210) a noise signal that is present in the PPG signal collected in the same time window. In an embodiment, the one or more hardware processors 102 of the system 100 performs a Principal Component Analysis (PCA) of the accelerometer signal to estimate the noise signal. The motion of the user can be approximated in a particular direction if a brief window of time is considered during which motion of the user is majorly unidirectional in an arbitrary direction. The PCA is applied on the accelerometer signal so as to find out which direction has a maximum variation in acceleration (due to the motion) the Principal Component Analysis (PCA) is applied to the acceleration signal. The PCA projects the original signal into orthonormal basis along which the variance is maximized. Assuming $Y \in \mathbb{R}^{T*3}$ is a projected matrix it is denoted as Y=AW where $A \in \mathbb{R}^{T*3}$ is an acceleration matrix and columns of the projection matrix $W \in \mathbb{R}^{3*3}$ represents eigenvector basis. As a first principle component of Y matrix highest variance among the three orthogonal direction, it is considered as the direction of motion or the noise. Noise spectrum is estimated as:

$$P_N(f) \approx PC1(f) \in \mathbb{R}^{1*M} \quad (1)$$

As the highest variance of accelerometer signal is itself a marker of motion, this approach improves the estimate of noise.

The one or more hardware processors 102 of the system 100 further estimates (212) value of a true cardiac signal for the time window. In the time windows in which motion has been detected, the true cardiac signal is not available, hence the estimation is required. Steps in method 300 involved in estimation of the true cardiac signal are depicted in FIG. 3. The system 100 maintains in the memory 101, a Clean Signal Buffer (CBF). The system 100 collects information pertaining to a pre-defined number (N) of spectra prior to the time window being considered for estimation of the true cardiac signal and stores this information in the CBF. In an embodiment, at any instance the CBF comprises data pertaining to PPG signal containing noise data for a time window being considered. In various embodiments, value of N is pre-configured or dynamically configured with the system 100 by an authorized user and is stored in the memory 101. For estimation of the true cardiac signal for the time window, the system 100 obtains (302) the spectra present in the CBF and estimates (304) value of the true cardiac signal as a trimmed mean of N number of spectra, which is represented as:

$$b_k = \frac{1}{N}\sum_{i=1}^{N} CB(i, k) \; \forall \, k \in [1, M] \quad (2)$$

$$P_C(f) \approx B = [b_1, ..., b_M] \in \mathbb{R}^{1*M}$$

Where M represents total number of frequency bins. Rows of the CBF contain envelops of previous N spectra. The estimation of the true cardiac signal is performed along the columns of the CBF for every frequency bin. This leads to a row vector $B \in \Lambda(1*M)$ which approximates the true cardiac spectrum. This averaging process smoothens the signal, imparts the uniformity and curtails the high-frequency noises. Since intense movement of the user could cause spurious noises, by taking the trimmed mean, outliers are eliminated. Later when the Weiner Filter estimates the clean PPG spectrum for that particular window the noisy PPG spectrum is replaced by the clean one.

The system 100 uses the following equation to obtain coefficients for the Wiener filter.

$$W_{opt}(f) = \frac{P_C(f)}{P_C(f) + P_N(f)} \quad (3)$$

After approximating the true cardiac spectrum and the noise spectrum, the system 100 applies (1) and (2) in (3) to obtain a final equation for Wiener filter coefficients as:

$$W_{opt}(f) = \frac{B}{B + PC_1(f)} \quad (4)$$

It is to be noted that in equation (4), all the elements are having same dimension ($\in \mathbb{R}^{1*M}$) and sample-wise divisions is achieved.

Based on the estimated coefficients, the Wiener filter of the system 100 estimates (214) a spectrum of clean PPG for the time window, based on the estimated noise signal and the true cardiac signals. The estimated spectrum of clean PPG is further used by the system 100 to estimate (216) heart rate of the user at the time window being considered.

In various embodiments, steps in method 200 may be performed in the same order as depicted in FIG. 2 or in any alternate order that is technically feasible. In another embodiment, one or more of the steps in method 200 may be omitted as per requirements.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of heart rate estimation of a user when the user is in motion. The embodiment thus provides a Wiener filter based mechanism to estimate heart rate of the user while in motion. Moreover, the embodiments herein further provide a mechanism to estimate a true cardiac signal for each time window in which user motion was detected, for the purpose of estimating a spectrum of clean PPG signal which in turn is used for heart rate estimation.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for heart rate estimation, comprising:
    collecting a photoplethysmogram (PPG) signal and an accelerometer signal over a plurality of fixed time windows related to a user being monitored, via one or more hardware processors;
    pre-processing the collected PPG signal and the accelerometer signal and performing filtering and normalization, via the one or more hardware processors;
    determining whether the user was in motion in any of the plurality of fixed time windows while the PPG signal was being collected, by performing a mobility detection, via the one or more hardware processors;
    classifying each of the plurality of fixed time windows as belonging to one of a set of time windows in which the user is determined to be in motion or a set of time windows in which the user is determined as not in motion; and
    performing the heart rate estimation for the PPG signal collected over each time window belonging to the set of time windows in which the user is determined as in motion, via the one or more hardware processors, wherein performing the heart rate estimation for the PPG signal comprises:
        estimating a noise signal by performing a Principal Component Analysis (PCA) of an accelerometer signal collected over each of the time windows in which the user is determined as being in motion, wherein the PCA is applied on the accelerometer signal to find out a direction that has a variation in acceleration due to the motion;
        estimating a value of a true cardiac signal for each of the time windows in which the user is determined as being in motion, wherein the true cardiac signal is the PPG signal without outliers and wherein estimating a value of the true cardiac signal comprises:
            obtaining a pre-defined number of spectra associated with the true cardiac signals prior to a time window being considered, from a Clean Signal Buffer (CBF); and
            estimating the value of the true cardiac signal by taking a trimmed mean of the obtained pre-defined number of spectra, wherein estimation of the value of the true cardiac signal enables approximation of a true cardiac spectrum, wherein the approximation initiates at least one of smoothening the PPG signal, and curtailment of high frequency noises and wherein the value of the true cardiac signal ($b_k$) is estimated by:

$$b_k = \frac{1}{N} \sum_{i=1}^{N} CB(i, k) \forall\, k \in [1, M],$$

wherein N represents the obtained pre-defined number of spectra and M represents a total number of frequency bins, wherein the estimation of the true cardiac signal is performed along columns of the CBF for each frequency bin of the total number of frequency bins;
        estimating a spectrum of a clean PPG signal based on the estimated noise signal and the estimated value of the true cardiac signal, using a Wiener filter; and
        estimating a heart rate of the user based on the estimated spectrum of the clean PPG signal.

2. The method of claim 1, wherein the CBF comprises the PPG signal collected from the user along with the obtained pre-defined number of spectra.

3. The method of claim 1, wherein in each time window in which the user is determined as not in motion, the heart rate is estimated from the collected PPG signal in a corresponding time window.

4. A system for heart rate estimation, comprising:
    one or more hardware processors;
    one or more communication interfaces; and
    one or more memory storing a plurality of instructions, wherein the plurality of instructions when executed cause the one or more hardware processors to:
        collect a photoplethysmogram (PPG) signal over a plurality of fixed time windows related to a user being monitored;
        pre-process the collected PPG signal and the accelerometer signal and perform filtering and normalization;
        determine whether the user was in motion in any of the plurality of fixed time windows while the PPG signal was being collected, by performing a mobility detection;
        classify each of the plurality of fixed time windows as belonging to one of a set of time windows in which the user is determined to be in motion or a set of time windows in which the user is determined as not in motion; and
        perform the heart rate estimation for the PPG signal collected over each time window belonging to the set of time windows in which the user is determined as in motion, by:
            estimating a noise signal by performing a Principal Component Analysis (PCA) of an accelerometer signal collected over each of the time windows in which the user is determined as being in motion wherein the PCA is applied on the accelerometer signal to find out a direction that has a variation in acceleration due to the motion;

estimating a value of a true cardiac signal for each of the time windows in which the user is determined as being in motion, wherein the true cardiac signal is the PPG signal without outliers and wherein estimating a value of the true cardiac signal comprises:

obtaining a pre-defined number of spectra associated with the true cardiac signals prior to a time window being considered, from a Clean Signal Buffer (CBF); and estimating the value of the true cardiac signal by taking a trimmed mean of the obtained pre-defined number of spectra, wherein estimation of the value of the true cardiac signal enables approximation of a true cardiac spectrum, wherein the approximation initiates at least one of smoothening the PPG signal, and curtailment of high frequency noises and wherein the value of the true cardiac signal ($b_k$) is estimated by:

$$b_k = \frac{1}{N}\sum_{i=1}^{N} CB(i, k) \forall\, k \in [1, M],$$

wherein N represents the obtained pre-defined number of spectra and M represents a total number of frequency bins, wherein the estimation of the true cardiac signal is performed along columns of the CBF for each frequency bin of the total number of frequency bins;

estimating a spectrum of a clean PPG signal based on the estimated noise signal and the estimated value of the true cardiac signal, using a Wiener filter; and estimating a heart rate of the user based on the estimated spectrum of the clean PPG signal.

5. The system of claim 4, wherein the CBF comprises the PPG signal collected from the user along with the obtained pre-defined number of spectra.

6. The system of claim 4, wherein the system estimates the heart rate of the user in each time window in which the user is determined as not in motion, from the collected PPG signal in a corresponding time window.

7. A non-transitory computer readable medium for heart rate estimation, wherein the non-transitory computer readable medium when executed by one or more hardware processors, causes the heart rate estimation by:

collecting a photoplethysmogram (PPG) signal over a plurality of fixed time windows related to a user being monitored, via one or more hardware processors;

pre-processing the collected PPG signal and the accelerometer signal and performing filtering and normalization, via the one or more hardware processors;

determining whether the user was in motion in any of the plurality of fixed time windows while the PPG signal was being collected, by performing a mobility detection, via the one or more hardware processors;

classifying each of the plurality of fixed time windows as belonging to one of a set of time windows in which the user is determined to be in motion or a set of time windows in which the user is determined as not in motion; and performing the heart rate estimation for the PPG signal collected over each time window belonging to the set of time windows in which the user is determined as in motion, via the one or more hardware processors, wherein performing the heart rate estimation for the PPG signal comprises:

estimating a noise signal by performing a Principal Component Analysis (PCA) of an accelerometer signal collected over each of the time windows in which the user is determined as being in motion, wherein the PCA is applied on the accelerometer signal to find out a direction that has a variation in acceleration due to the motion;

estimating a value of a true cardiac signal for each of the time windows in which the user is determined as being in motion, wherein the true cardiac signal is the PPG signal without outliers and wherein estimating a value of the true cardiac signal comprises:

obtaining a pre-defined number of spectra associated with the true cardiac signals prior to a time window being considered, from a Clean Signal Buffer (CBF); and estimating the value of the true cardiac signal by taking a trimmed mean of the obtained pre-defined number of spectra, wherein estimation of the value of the true cardiac signal enables approximation of a true cardiac spectrum, wherein the approximation initiates at least one of smoothening the PPG signal, and curtailment of high frequency noises and wherein the value of the true cardiac signal ($b_k$) is estimated by:

$$b_k = \frac{1}{N}\sum_{i=1}^{N} CB(i, k) \forall\, k \in [1, M],$$

wherein N represents the obtained pre-defined number of spectra and M represents a total number of frequency bins, wherein the estimation of the true cardiac signal is performed along columns of the CBF for each frequency bin of the total number of frequency bins;

estimating a spectrum of a clean PPG signal based on the estimated noise signal and the estimated value of the true cardiac signal, using a Wiener filter; and estimating a heart rate of the user based on the estimated spectrum of the clean PPG signal.

8. The non-transitory computer readable medium of claim 7, wherein the CBF comprises the PPG signal collected from the user along with the obtained pre-defined number of spectra.

9. The non-transitory computer readable medium of claim 7, wherein in each time window in which the user is determined as not in motion, the heart rate is estimated from the collected PPG signal in a corresponding time window.

* * * * *